(12) United States Patent
Mu et al.

(10) Patent No.: US 12,384,956 B2
(45) Date of Patent: Aug. 12, 2025

(54) METHOD FOR INHIBITING BIOGENIC HYDROGEN SULFIDE IN OILFIELDS

(71) Applicant: EAST CHINA UNIVERSITY OF SCIENCE AND TECHNOLOGY, Shanghai (CN)

(72) Inventors: Bozhong Mu, Shanghai (CN); Lei Zhou, Shanghai (CN); Yifan Liu, Shanghai (CN); Shizhong Yang, Shanghai (CN); Jun Wu, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 18/713,690

(22) PCT Filed: Jun. 7, 2023

(86) PCT No.: PCT/CN2023/098741
§ 371 (c)(1),
(2) Date: May 27, 2024

(87) PCT Pub. No.: WO2023/246505
PCT Pub. Date: Dec. 28, 2023

(65) Prior Publication Data
US 2025/0026976 A1 Jan. 23, 2025

(30) Foreign Application Priority Data
Jun. 23, 2022 (CN) .......................... 202210719843.1

(51) Int. Cl.
*C09K 8/54* (2006.01)
*C12N 1/20* (2006.01)
(Continued)

(52) U.S. Cl.
CPC ................ *C09K 8/54* (2013.01); *C12N 1/205* (2021.05); *C12Q 1/04* (2013.01); *C09K 2208/32* (2013.01); *C12R 2001/01* (2021.05)

(58) Field of Classification Search
CPC ...... C09K 8/54; C09K 2208/32; C12N 1/205; C12Q 1/04; C12R 2001/01
See application file for complete search history.

(56) References Cited

U.S. PATENT DOCUMENTS

2020/0123433 A1    4/2020   Faremer et al.

FOREIGN PATENT DOCUMENTS

| CN | 101313681 | 12/2008 |
| CN | 105236538 | 1/2016 |

(Continued)

OTHER PUBLICATIONS

Bo Zhao et al., "Microbial Control of Sulfate-reducing Bacteria", Reviews, Aug. 18, 2012, with English abstract, pp. 74-79, vol. 30, No. 23.

(Continued)

*Primary Examiner* — Louise W Humphrey
*Assistant Examiner* — Rachel Emily Martin
(74) *Attorney, Agent, or Firm* — JCIPRNET

(57) ABSTRACT

The present invention relates to a method for inhibiting biogenic hydrogen sulfide in oilfields. A synergistic inhibition system combination agent containing *Geobacillus* strain GW1 is added into oilfield systems, wherein the strain GW1 has been deposited in China General Microbiological Culture Collection Center on Oct. 20, 2021, and has the deposit number of CGMCC No. 23631.

9 Claims, 1 Drawing Sheet

(51) Int. Cl.
*C12Q 1/04* (2006.01)
*C12R 1/01* (2006.01)

(56) References Cited

FOREIGN PATENT DOCUMENTS

| CN | 105660705 | 6/2016 |
| CN | 109182211 | 1/2019 |
| CN | 111378592 | 7/2020 |
| CN | 111997582 | 11/2020 |
| CN | 112342167 | 2/2021 |
| CN | 115161001 | 10/2022 |
| KR | 20120088498 | 8/2012 |
| WO | 9612867 | 5/1996 |

OTHER PUBLICATIONS

E. Korenblum et al., "Production of antimicrobial substances by Bacillus subtilis LFE-1, B. firmus H2O-1 and B. licheniformis T6-5 isolated from an oil reservoir in Brazil", Journal of Applied Microbiology, Jan. 19, 2005, pp. 667-675, vol. 98, No. 3.

H.S. El-Sheshtawy et al., "Production of biosurfactant from Bacillus licheniformis for microbial enhanced oil recovery and inhibition the growth of sulfate reducing bacteria", Egyptian Journal of Petroleum, Jun. 19, 2015, pp. 155-162, vol. 24.

Weisheng Guan et al., "The Making Progress of the Anaerobic Biological Process Treatment of Organic Wastewater Containing Sulfate", China Biogas, May 28, 1995, with English abstract, pp. 1-3, vol. 13, No. 2.

"International Search Report (Form PCT/ISA/210) of PCT/CN2023/098741", mailed on Sep. 7, 2023, with English translation thereof, pp. 1-6.

"Written Opinion of the International Searching Authority (Form PCT/ISA/237) of PCT/CN2023/098741", mailed on Sep. 7, 2023, pp. 1-5.

METHOD FOR INHIBITING BIOGENIC HYDROGEN SULFIDE IN OILFIELDS

CROSS-REFERENCE TO RELATED APPLICATION

This application is a 371 application of International PCT application serial no. PCT/CN2023/098741 filed on Jun. 7, 2023, which claims the priority benefit of China application no. 202210719843.1 filed on Jun. 23, 2022. The entirety of each of the above-mentioned patent applications is hereby incorporated by reference herein and made a part of this specification.

TECHNICAL FIELD

The present disclosure relates to the field of microbial influenced corrosion control in oil reservoir environments, and in particular to a method for inhibiting biogenic hydrogen sulfide in oilfields.

DESCRIPTION OF RELATED ART

In the oilfield systems, the growth and metabolic activities of some microorganisms cause a serious of problems such as petroleum pipeline corrosion, reservoir blockage, environmental pollution, etc. It was reported that the annual cost of corrosion in the world was about 4 trillion dollars, of which the economic loss caused by microbial influenced corrosion accounted for about 20%. There have been approximately 7,000 leakage events in Nigerian oilfields in 35 years, with the losses amounting to 200 million dollars. This means that an average of 200 cases of leakage occur every year, and the leakage rate is the highest in the world. Under anoxic conditions, such as in wells and pipelines, sulfate-reducing microorganisms are usually considered to be the main contributors causing oil reservoir souring and pipeline corrosion. Therefore, the adverse effects caused by the sulfate-reducing microorganisms are one of the problems that must be faced and urgently need to be solved during oilfield development.

Since corrosion caused by sulfate-reducing microorganisms can bring many negative effects, the petroleum industry has begun to use various mitigation strategies to control oil reservoir souring, among which biological methods are the commonly used inhibitory measures for oilfield corrosion control. Since the 1980s, GMT-LATA Company has begun to study the injection of nitrate into anaerobic oil and gas production systems. They found that hydrogen sulfide significantly decreased and the nitrate-reducing bacteria had inhibition effect on the metabolic activities of the sulfate-reducing microorganisms.

However, for the current control of biogenic hydrogen sulfide in oil reservoir environments, there are still some problems such as low inhibition ratio, complex injection system and high economic cost, etc.

SUMMARY

The objective of the present disclosure is to provide a method for inhibiting biogenic hydrogen sulfide in oilfields, in order to overcome the aforementioned deficiencies in the prior art. The synergistic inhibition effect of a microbe and an inhibiting agent is adopted to better reduce the corrosion impact caused by hydrogen sulfide.

During the conception process, the applicants have made the following analysis: compared with the chemical method of adding chemical biocides, the biological competition method of inhibiting sulfate-reducing microorganisms by utilizing nitrate-reducing bacteria has attracted attention because of its environmental friendliness and no secondary pollution. Therefore, it is important to obtain the nitrate-reducing strains with excellent performance and construct the inhibition systems with obvious inhibition effect for the inhibition of the sulfate-reducing microorganisms in oilfield systems.

The objective of the present disclosure can be achieved by the following technical solution.

The objective of the present disclosure is to provide a method for controlling biogenic hydrogen sulfide in oilfields for protection, including adding a synergistic inhibition system containing the strain GW1 (*Geobacillus stearothermophilus*) into oilfield systems.

The strain GW1 (*Geobacillus stearothermophilus*) has been deposited in China General Microbiological Culture Collection Center on Oct. 20, 2021 with the deposit number of CGMCC No. 23631.

Further, the strain GW1 (*Geobacillus stearothermophilus*) has been obtained by screening and culturing from the oilfield production water.

Further, the synergistic inhibition system also includes an activator and a synergistic inhibitor.

Further, the activator is sodium nitrate, and the synergistic inhibitor is barium chloride.

Further, the screening process of the strain GW1 (*Geobacillus stearothermophilus*) includes: taking the oilfield production water as an inoculation source, carrying out strain isolation by anaerobic roll-tube method of Hungate, incubating anaerobic tubes in a 55° C. oven away from light for 2 weeks, and then picking individual colonies and identifying.

Further, the culture conditions of the strain GW1 (*Geobacillus stearothermophilus*) include the following components.

5.00 g/L of NaCl, 0.28 g/L of $MgCl_2 \cdot 6H_2O$, 0.55 g/L of $CaCl_2$, 0.24 g/L of $NH_4Cl$, 0.10 g/L of KCl, 1.50 g/L of sodium acetate, 0.85 g/L of $NaNO_3$, 0.20 g/L of $NaHCO_3$, 0.20 g/L of $KH_2PO_4$ and 1.0 mL/L of trace elements.

The suitable growth temperature of 30° C.-60° C., and the optimal growth temperature of 50° C.-55° C.

Further, the trace elements include the following components.

1.20 g/L of HCl (25%), 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$.

Further, the process of adding the synergistic inhibition system containing the strain GW1 into the oilfield system is: adding the strain GW1 and the activator sodium nitrate to a target location inhabited by sulfate-reducing microorganisms, and further adding barium chloride as a synergistic inhibitor on the basis of the aforementioned system.

Wherein the inoculation amount of the strain GW1 transferred to the target location is 5%-9%.

Further, the added amount of sodium nitrate as the activator is 0.30-0.80 g/L, and the added amount of barium chloride as the synergistic inhibitor is 1.50-3.00 g/L, and the optimal concentration is 0.60 g/L.

Further, the concentration ratio of barium chloride to sulfate ions in the water sample, $C_{barium\ chloride} : C_{sulfate\ ions} = 1:1-2:1$, or the concentration of barium chloride is 1.50 g/L-3.00 g/L, and the optimal concentration is 2.00 g/L.

Compared with the prior art, the present disclosure has the following technical advantages.

1) The present disclosure provides a method for inhibiting hydrogen sulfide by utilizing the strain GW1 and the synergistic inhibition system, which can effectively reduce the content of hydrogen sulfide in the oilfield water. The system of the strain GW1 and the activator sodium nitrate provided by the present disclosure has a hydrogen sulfide inhibition ratio of greater than 90.81%. Further adding barium chloride as the synergistic inhibitor on the basis of the aforementioned system can have a significant inhibition effect on hydrogen sulfide in the systems, with the hydrogen sulfide inhibition ratio up to 99.37%.

2) The present disclosure has innovatively discovered the strain GW1, which can effectively control sulfate-reducing microorganisms in oilfield systems. The cell density of the strain shows an increasing trend at the initial stage of culture, and the increase rate slows down with the extension of culture time, reaching equilibrium at Day 18. Meanwhile, after 16 days of culture, nitrate in the systems has been almost completely consumed, indicating that the isolated strain can effectively utilize nitrate for growth and metabolism.

3) The system containing the inhibition bacteria GW1 in the present disclosure can effectively inhibit the content of hydrogen sulfide in the systems. Moreover, the strain has a synergistic inhibition effect with barium chloride. The system has obvious application effect and is easy to operate, and has good application prospects in corrosion control of oilfield systems.

DESCRIPTION OF THE EMBODIMENTS

Figure 1:
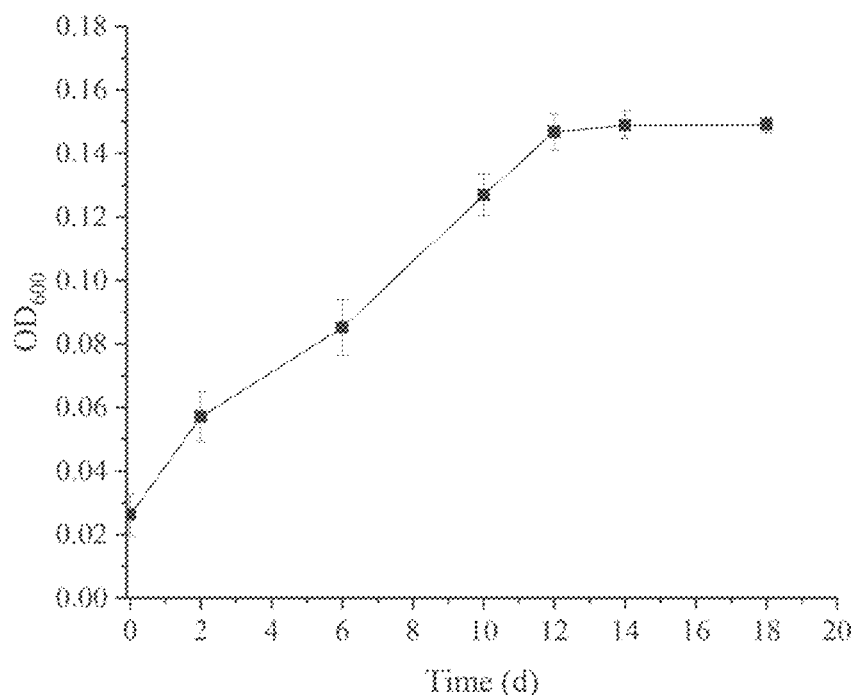
FIG. 1 shows the $OD_{600}$ growth curve of the strain GW1.

In the present disclosure, the synergistic inhibition effect of a microbe and an inhibiting agent is adopted to better reduce the corrosion impact caused by hydrogen sulfide. The strain GW1 (*Geobacillus stearothermophilus*) is provided, which has been deposited in China General Microbiological Culture Collection Center on Oct. 20, 2021 with the deposit number of CGMCC No. 23631. Specifically, a synergistic inhibition system containing the strain GW1 (*Geobacillus stearothermophilus*) is added into oilfield systems. There is the synergistic inhibition effect between the strain and barium chloride. The system has obvious application effects and is easy to operate, and has good application prospects in corrosion control of oilfield systems. In detail, the biological materials, *Geobacillus stearothermophilus* GW1, in the present application has been deposited under the Budapest Treaty at China General Microbiological Culture Collection Center (CGMCC) on Oct. 20, 2021, and assigned Accession Number 23631. This deposit ensures that the material will be irrevocably and without restriction available to the public upon the grant of a patent in this application. The deposit will be maintained for a period of at least 30 years, or 5 years after the last request for a sample, whichever is longer.

The present disclosure will be described in detail hereafter with reference to the attached figures and specific embodiments. The features such as preparation means, materials, structures or compositions that are not clearly stated in the present technical solution, are regarded as common technical features disclosed in the prior art.

Example 1

This example was a verification example of the strain isolation.

When sampling was conducted from Well W1 of Jiangsu oilfield, oil-water sample was collected into a 50-L sterilized plastic bucket. The production water was concentrated into sterilized serum bottles by an ultrafiltration concentrator within 30 min. The serum bottles were placed in an incubator filled with dry ice and quickly transported back to the laboratory for further processing.

The needle of a sterile syringe was inserted into the nitrogen outlet device, and sucked for 3-5 times for gas replacement. Then 0.1 mL of the production water was absorbed and added into an anaerobic tube pre-filled with 0.9 mL of sterile and oxygen-free water. By analogy, the water sample was successively diluted into dilutions with different concentrations of $10^{-1}$, $10^{-2}$, $10^{-3}$, $10^{-4}$ and $10^{-5}$, and then subjected to the isolation of single strains with the anaerobic roll-tube method of Hungate. The culture medium used for isolation included: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 1.50 g/L of sodium acetate, 0.85 g/L of $NaNO_3$, 0.20 g/L of $NaHCO_3$, 0.20 g/L of $KH_2PO_4$ and 1.0 mL/L of trace elements. The trace element formula was: 1.20 g/L of HCl (25%), 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$.

The isolated strain was identified by molecular biology method, and the 16S rDNA fragments of the strain were amplified by using the following bacterial primers: 27F: 5'-AGAGTTTGATCCTGGCTCAG-3' and 1492R: 5'-GGTTACCTTGTTACGACTT-3'. The amplified sequences were sequenced and aligned. The screened nitrate-reducing strain belonged to *Geobacillus* (*Geobacillus stearothermophilus*) taxonomically, and was named GW1. The bacterial solution was pipetted and added to glycerol (30%, v/v), and then stored at −80° C.

Example 2

This example was a verification example of the growth and metabolism

Figure 2:
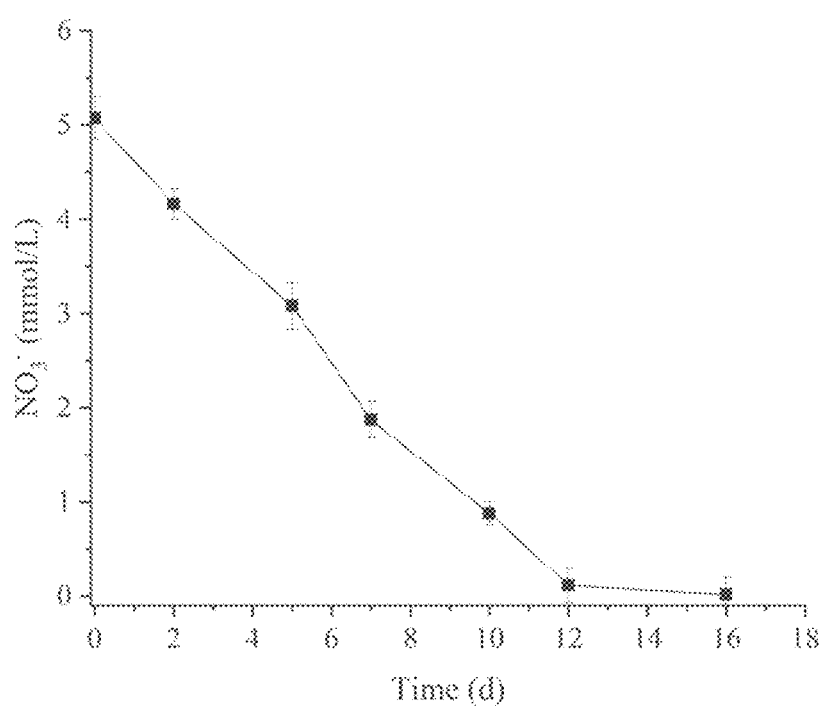
FIG. 2 shows the consumption of $NO_3^-$ by the strain GW1.

The strain GW1 screened in Example 1 was inoculated into 20 mL of the culture medium, and incubated anaerobically at 55° C. The composition of the culture medium was: 5.00 g/L of NaCl, 0.28 g/L of $MgCl_2 \cdot 6H_2O$, 0.55 g/L of $CaCl_2$, 0.24 g/L of $NH_4Cl$, 0.10 g/L of KCl, 1.50 g/L of sodium acetate, 0.85 g/L of $NaNO_3$, 0.20 g/L of $NaHCO_3$, 0.20 g/L of $KH_2PO_4$ and 1.0 mL/L of trace elements. The trace element formula was: 1.20 g/L of HCl (25%), 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$. As shown in FIG. 1 and FIG. 2, the cell concentration and nitrate consumption after diluting the strain culture sample by 10 times were respectively. The results showed that the strain grew well at 55° C., and the cell concentration ($OD_{600}$) reached greater than 1.5 after 18 days of culture. After 16 days of culture, nitrate in the systems was almost completely consumed, indicating that the isolated strain could utilize nitrate for growth and metabolism.

Example 3

This example was an application example of the strain and the synergistic inhibition system.

The deposited GW1 was inoculated into the culture medium (with the composition of the culture medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 1.50 g/L of sodium acetate, 0.85 g/L of $NaNO_3$, 0.20 g/L of $NaHCO_3$, 0.20 g/L of $KH_2PO_4$ and 1.0 mL/L of trace elements. The trace element formula was: 1.20 g/L of HCl (25%), 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$). The pH was adjusted to 7.0, and anaerobically incubated at 30° C. for 16 days.

The production water from Xinjiang oilfield was inoculated into the culture medium for enriching sulfate-reducing microorganisms (with the composition of the culture medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 0.20 g/L of $KH_2PO_4$, 2.00 g/L of sodium lactate, 1.42 g/L of $Na_2SO_4$ and 0.20 g/L of $NaHCO_3$). The pH was adjusted to 7.0 and the culture was incubated at 30° C. for 7 days to obtain the fresh enrichment culture of the sulfate-reducing microorganisms.

The enrichment culture of the sulfate-reducing microorganisms was inoculated into the basal medium with a ratio of 5% (with the composition of the medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 0.20 g/L of $KH_2PO_4$, 2.00 g/L of sodium lactate, 2.00 g/L of $Na_2SO_4$ and 2.50 g/L of $NaHCO_3$). Then the strain GW1 with the inoculation proportion of 5% and an agent (0.30 g/L of sodium nitrate) were added. Meanwhile, the control group without addition of the inhibition system was set, i.e., the control group only inoculated with the enrichment culture of the sulfate-reducing microorganisms. Each group included triplicates. After 16 days of culture at 30° C., it was found that the inhibition ratio of hydrogen sulfide was approximately 90.81%. On the basis, 2.00 g/L of barium chloride as the synergistic inhibitor was added, and the inhibition ratio of hydrogen sulfide reached approximately 95.15%.

Example 4

This example was an application example of the strain and the synergistic inhibition system.

The deposited GW1 was inoculated into the culture medium (with the composition of the culture medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 1.50 g/L of sodium acetate, 0.85 g/L of $NaNO_3$, 0.20 g/L of $NaHCO_3$, 0.20 g/L of $KH_2PO_4$ and 1.0 mL/L of trace elements. The trace element formula was: 1.20 g/L of HCl (25%), 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$). The pH was adjusted to 7.0, and anaerobically incubated at 55° C. for 16 days.

The production water from Shengli oilfield was inoculated into the culture medium for enriching sulfate-reducing microorganisms (with the composition of the culture medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 0.20 g/L of $KH_2PO_4$, 2.00 g/L of sodium lactate, 1.42 g/L of $Na_2SO_4$ and 0.20 g/L of $NaHCO_3$). The pH was adjusted to 7.0 and the culture was incubated at 55° C. for 7 days to obtain the fresh enrichment culture of the sulfate-reducing microorganisms.

The enrichment culture of the sulfate-reducing microorganisms was inoculated into the basal medium with a ratio of 5% (with the composition of the medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 0.20 g/L of $KH_2PO_4$, 2.00 g/L of sodium lactate, 1.50 g/L of $Na_2SO_4$ and 2.50 g/L of $NaHCO_3$). Then the strain GW1 with the inoculation proportion of 7% and an agent (0.80 g/L of sodium nitrate) were added. Meanwhile, the control group without addition of the inhibition system was set, i.e., the control group only inoculated with the enrichment culture of the sulfate-reducing microorganisms. Each group included triplicates. After 14 days of culture at 55° C., it was found that the inhibition ratio of hydrogen sulfide was 91.68%. On the basis, 3.00 g/L of barium chloride as the synergistic inhibitor was added, and the inhibition ratio of hydrogen sulfide reached 96.27%.

Example 5

This example was an application example of the strain and the synergistic inhibition system.

The deposited GW1 was inoculated into the culture medium (with the composition of the culture medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 1.50 g/L of sodium acetate, 0.85 g/L of $NaNO_3$, 0.20 g/L of $NaHCO_3$, 0.20 g/L of $KH_2PO_4$ and 1.0 mL/L of trace elements. The trace element formula was: 1.20 g/L of HCl (25%), 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$). The pH was adjusted to 7.0, and anaerobically incubated at 50° C. for 16 days.

The production water from Daqing oilfield was inoculated into the culture medium for enriching sulfate-reducing microorganisms (with the composition of the culture medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 0.20 g/L of $KH_2PO_4$, 2.00 g/L of sodium lactate, 1.42 g/L of $Na_2SO_4$ and 0.20 g/L of $NaHCO_3$). The pH was adjusted to 7.0 and the culture was incubated at 50° C. for 7 days to obtain the fresh enrichment culture of the sulfate-reducing microorganisms.

The enrichment culture of the sulfate-reducing microorganisms was inoculated into the basal medium with a ratio of 5% (with the composition of the medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 0.20 g/L of $KH_2PO_4$, 2.00 g/L of sodium lactate, 1.00 g/L of $Na_2SO_4$ and 2.50 g/L of $NaHCO_3$). Then the strain GW1 with the inoculation proportion of 9% and an agent (0.60 g/L of sodium nitrate) were added. Meanwhile, the control group without addition of the inhibition system was set, i.e., the control group only inoculated with the enrichment culture of the sulfate-reducing microorganisms. Each group included triplicates. After 12 days of culture at 50° C., it was found that the inhibition ratio of hydrogen sulfide was 93.56%. On the basis. 1.50 g/L of barium chloride as the synergistic inhibitor was added, and the inhibition ratio of hydrogen sulfide reached 99.37%.

Example 6

This example was an application example of the strain and the synergistic inhibition system.

The deposited GW1 was inoculated into the culture medium (with the composition of the culture medium: 5.00 g/L of NaCl, 0.28 g/L of $MgCl_2 \cdot 6H_2O$, 0.55 g/L of $CaCl_2$), 0.24 g/L of $NH_4Cl$, 0.10 g/L of KCl, 1.50 g/L of sodium acetate, 0.85 g/L of $NaNO_3$, 0.20 g/L of $KH_2PO_4$, 0.20 g/L of $NaHCO_3$ and 1.0 mL/L of trace elements. The trace element formula was: 1.20 g/L of HCl (25%), 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$). The pH was adjusted to 7.0, and anaerobically incubated at 60° C. for 16 days.

The strain GW1 was inoculated into the production water of Jiangsu oilfield with a proportion of 9%, and an agent (0.50 g/L of sodium nitrate) was also added. Meanwhile, the control group without addition of the inhibition system was set. Each group included triplicates. After 14 days of culture at 60° C. it was found that the inhibition ratio of hydrogen sulfide was 93.19%. On the basis, 3.00 g/L of barium chloride as the synergistic inhibitor was added, and the inhibition ratio of hydrogen sulfide reached 99.06%.

In summary, the present disclosure provides a method for inhibiting hydrogen sulfide by utilizing the strain GW1 and the synergistic inhibition system, which can effectively reduce the content of hydrogen sulfide in the fluid of the oilfield systems. The system of the strain GW1 and the activator sodium nitrate as provided by the present disclosure has the inhibition ratio of hydrogen sulfide greater than 90.81%. On the basis of the aforementioned system, further adding barium chloride as the synergistic inhibitor can have significant inhibition effect on hydrogen sulfide in the systems, with the inhibition ratio of hydrogen sulfide up to 99.37%. The present disclosure has innovatively discovered the strain GW1, which can effectively control sulfate-reducing microorganisms in oilfield systems. The cell density of the strain showed an increasing trend at the initial stage of culture, and with the extension of culture time, the increase rate slowed down and reached equilibrium at Day 18. Meanwhile, after 16 days of culture, nitrate in the systems was almost completely consumed, indicating that the isolated strain could utilize nitrate for growth and metabolism.

During the verification process of the inhibition system provided by the present disclosure, the growth environment of the sulfate-reducing microorganisms in the oilfield system was simulated, including temperature, pH, electron donors and electron acceptors possibly present in the metabolic process of the sulfate-reducing microorganisms. Meanwhile, the sulfate-reducing microorganisms in production water were also subjected to expanded culture. Therefore, the inhibition system constructed by the present application can be directly applied to inhibit hydrogen sulfide produced by sulfate-reducing microorganisms in oilfield systems.

The above description of the embodiments is intended to facilitate the understanding and use of the present disclosure by persons generally skilled in the technical field. It is obvious that those skilled in the art can easily make various modifications to these embodiments and apply the general principles described herein to other embodiments without inventive efforts. Therefore, the present disclosure is not limited to the aforementioned embodiments. Based on the disclosure of the present invention, all of the improvements and modifications made by those skilled in the art without departing from the scope of the present disclosure, should be within the claimed scope of the present disclosure.

What is claimed is:

1. A method for inhibiting biogenic hydrogen sulfide accumulation in oilfields, comprising adding a synergistic inhibition system containing a *Geobacillus stearothermophilus* strain GW1 into an oilfield system;
    wherein the GW1 strain has been deposited in the China General Microbiological Culture Collection Center (CGMCC) under deposit number 23631,
    wherein the synergistic inhibition system further comprises sodium nitrate as an activator and barium chloride as a synergistic inhibitor.

2. The method according to claim 1, wherein the GW1 strain is obtained by:
    isolating the GW1 strain from oilfield production water; and
    culturing the isolated GW1 strain.

3. The method according to claim 2, wherein isolating the GW1 strain comprises:
    collecting oilfield production water containing the GW1 strain as an inoculation source;
    culturing the strain using an anaerobic roll-tube method;
    incubating anaerobic tubes in a 55° C. oven away from light for 2 weeks; and
    identifying and picking individual GW1 colonies.

4. The method according to claim 2, wherein culturing the GW1 strain comprises:
    inoculating the GW1 strain isolated from oilfield production water and growing at a temperature of 30° C.-60° C. in a culture medium comprising: 5.00 g/L of NaCl, 0.28 g/L of $MgCl_2 \cdot 6H_2O$, 0.55 g/L of $CaCl_2$, 0.24 g/L of $NH_4Cl$, 0.10 g/L of KCl, 1.50 g/L of sodium acetate, 0.85 g/L of $NaNO_3$, 0.20 g/L of $NaHCO_3$, 0.20 g/L of $KH_2PO_4$ and 1.0 mL/L of trace elements.

5. The method according to claim 4, wherein the trace elements comprise:
    1.20 g/L of 25% HCl, 0.20 g/L of $NiCl_2 \cdot 6H_2O$, 0.10 g/L of $CaCl_2 \cdot 2H_2O$, 1.50 g/L of $FeCl_2 \cdot 4H_2O$, 0.50 g/L of $MnCl_2 \cdot 4H_2O$, 0.02 g/L of $H_3BO_3$, 0.01 g/L of $Na_2MoO_4 \cdot 2H_2O$, 0.50 g/L of $CoCl_2 \cdot 6H_2O$, 0.50 g/L of $ZnCl_2$ and 0.01 g/L of $AlCl_3$.

6. The method according to claim 1, wherein adding the synergistic inhibition system containing the *Geobacillus stearothermophilus* strain GW1 into the oilfield system comprises:
    adding the GW1 strain and the sodium nitrate to a target location inhabited by sulfate-reducing microorganisms; and
    adding the barium chloride.

7. The method according to claim 6, wherein the sodium nitrate is added in an amount of 0.3-0.8 g/L, and the barium chloride is added in an amount of 1.5-3.0 g/L.

8. The method according to claim 7, wherein a concentration ratio of barium chloride to sulfate ions in the target location is 1:1-2:1.

9. The method according to claim 4, wherein an optimal growth temperature of the GW1 strain is 50° C.-55° C.

* * * * *